(12) United States Patent
Abdellatif et al.

(10) Patent No.: US 11,454,572 B2
(45) Date of Patent: Sep. 27, 2022

(54) METHOD OF PLACING GAS SENSORS ON DRONES TO BENEFIT FROM THRUST AIR FLOW VIA PLACEMENT AND SCOOPS

(71) Applicant: Saudi Arabian Oil Company, Dhahran (SA)

(72) Inventors: Fadl Abdellatif, Thuwal (SA); Brian Parrott, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 16 days.

(21) Appl. No.: 16/893,177

(22) Filed: Jun. 4, 2020

(65) Prior Publication Data

US 2021/0381934 A1    Dec. 9, 2021

(51) Int. Cl.
*G01N 1/22*       (2006.01)
*B64C 39/02*      (2006.01)

(52) U.S. Cl.
CPC ......... *G01N 1/2273* (2013.01); *B64C 39/024* (2013.01); *B64C 2201/027* (2013.01); *B64C 2201/108* (2013.01); *B64C 2201/12* (2013.01)

(58) Field of Classification Search
CPC ............. G01N 1/2273; G01N 33/0006; G01N 2001/2279; G01N 2001/2291; G01N 33/0011; B64C 39/024; B64C 2201/027; B64C 2201/108; B64C 2201/12; B64C 21/02; B64C 9/14
See application file for complete search history.

(56) References Cited

U.S. PATENT DOCUMENTS

| | | | |
|---|---|---|---|
| 4,836,473 A | 6/1989 | Aulehla et al. | |
| 8,128,037 B2 | 3/2012 | Powell et al. | |
| 8,820,762 B2 | 9/2014 | Endo | |
| 8,852,950 B2 | 10/2014 | Hoyer et al. | |
| 2003/0058919 A1 | 3/2003 | Ice et al. | |

(Continued)

FOREIGN PATENT DOCUMENTS

| | | |
|---|---|---|
| CN | 102625909 A | 8/2012 |
| CN | 109187117 A | 1/2019 |

(Continued)

OTHER PUBLICATIONS

Villa, Tommaso Francesco, et al. "Development and validation of a UAV based system for air pollution measurements." Sensors 16.12 (2016): 2202. 15 pages.

(Continued)

*Primary Examiner* — Benjamin R Schmitt
(74) *Attorney, Agent, or Firm* — Leason Ellis LLP

(57) ABSTRACT

A multirotor drone comprises a main body and an air channel embedded within the main body having an air inlet on the surface of the main body, multiple propellers that induce an air flow toward the air inlet and into the air channel, a microcontroller positioned and configured to control navigation of the drone by actuation of the plurality of propellers, an air scoop having a section positioned at the outer surface of the main body adjacent to the air inlet which is adjustable so as to capture and divert air into the air inlet and air channel or to block air flow into the air inlet, and a gas sensor positioned within the air channel. The air scoop is positioned to capture air flow from at least one of the plurality of propellers into the air channel and to the gas sensor.

5 Claims, 10 Drawing Sheets

(56) References Cited

U.S. PATENT DOCUMENTS

| | | | |
|---|---|---|---|
| 2003/0132344 A1* | 7/2003 | Johnson | B64D 13/00 |
| | | | 244/118.5 |
| 2014/0238100 A1 | 8/2014 | Londergan et al. | |
| 2016/0152345 A1* | 6/2016 | Molnar | B64D 47/04 |
| | | | 244/39 |
| 2017/0267372 A1 | 9/2017 | Donnard et al. | |
| 2017/0341749 A1 | 11/2017 | Herber et al. | |
| 2018/0127093 A1 | 5/2018 | Christensen et al. | |
| 2018/0136093 A1 | 5/2018 | Avakov | |
| 2020/0019168 A1 | 1/2020 | Guzman et al. | |
| 2020/0033157 A1* | 1/2020 | Kaufman | G01C 23/005 |

FOREIGN PATENT DOCUMENTS

| | | | |
|---|---|---|---|
| CN | 110979677 A | 4/2020 | |
| EP | 1327581 A2 | 7/2003 | |
| EP | 3225546 A1 | 10/2017 | |
| JP | 2019200116 A | 11/2019 | |
| KR | 101841706 B1 | 3/2018 | |

OTHER PUBLICATIONS

Kuantama, Endrowednes, et al. "The Design and Experimental Development of Air Scanning Using a Sniffer Quadcopter." Sensors 19.18 (2019): 3849. 18 pages.

Sato, Ryohei, et al. "Detection of Gas Drifting Near the Ground by Drone Hovering Over: Using Airflow Generated by Two Connected Quadcopters." Sensors 20.5 (2020): 1397. 16 pages.

Lazik, Detlef. "Membrane-based characterization of a gas component—A transient sensor theory." Sensors 14.3 (2014): 4599-4617.

Bartholmai, Matthias, et al. "Micro-Drone for Gas Measurement in Hazardous Scenarios via Remote Sensing," Sensors, Jan. 1, 2010, 4 pages.

International Search Report and Written Opinion in corresponding PCT Application No. PCT/US2021/035896, dated Nov. 17, 2021.

International Search Report and Written Opinion in corresponding PCT Application No. PCT/US2021/035911, dated Sep. 24, 2021.

International Search Report and Written Opinion in corresponding PCT Application No. PCT/US2021/035915, dated Sep. 24, 2021.

Office Action in corresponding U.S. Appl. No. 16/893,252, dated Jun. 2, 2022; 23 pages.

* cited by examiner

METHOD OF PLACING GAS SENSORS ON DRONES TO BENEFIT FROM THRUST AIR FLOW VIA PLACEMENT AND SCOOPS

CROSS-REFERENCE TO RELATED APPLICATIONS

The present application relates to two other patent applications entitled, "Improved Gas Sensing for Fixed Wing Drones using Scoops" and "Calibration Methods for Gas Sensors Mounted In-Stream of Drone Propeller Airflow," respectively, which are being filed concurrently with the present disclosure.

FIELD OF THE DISCLOSURE

The present disclosure relates generally to methods and apparatus for enhancing air flow to gas sensors incorporated in drones, improving their sensitivity and accuracy. More particularly, the disclosure relates to a drone and a method for increasing air flow to a gas sensor disposed in an embedded air channel using adjustable air scoops.

BACKGROUND OF THE DISCLOSURE

Drones can be usefully applied to monitoring tasks such as detection of hazardous particulates and gases as they can autonomously travel to desired locations, such as industrial facilities, at which monitoring is desired. Such drones can be equipped with detectors and sensors that enable the drones to detect gasses at very low concentrations. The sensors generate data which can be transmitted electronically to a drone operator or other station. The data can provide useful indicators. For instance, the data can concern current plant conditions and safety. Safety monitoring is particularly relevant in oil and gas installations having environments with corrosive and/or flammable gases. Even at low concentrations, such hazardous gas can represent risk of explosion or other safety accidents, and, at a minimum, provide important inspection-related information.

Drones have typically been equipped with gas sensors by appending the sensors from booms or fixtures supported by the body or wings of the drone. However, appending the gas sensors in this external manner can leave the drone sensors exposed to uneven and uncontrollable air flow which distorts the detection profile and which can reduce detection sensitivity. In particular, the external sensor placements do not harness the capabilities of the drone flight characteristics to increase gas detection sensitivity.

SUMMARY OF THE DISCLOSURE

The present disclosure provides a multirotor drone that comprises a main body having an outer surface, and an air channel embedded within the main body having an upstream end at an air inlet at the outer surface of the main body, a plurality of propellers coupled to the outer surface of the main body, wherein actuation of at least one of the plurality of propellers induces an air flow directed toward the air inlet and into the air channel, a microcontroller positioned within the main body configured to control navigation of the drone by actuation of the plurality of propellers, an air scoop having a section positioned at the outer surface of the main body adjacent to the air inlet, the air scoop being adjustable between a first position to capture and divert air into the air inlet and thereby to the air channel and a second position to block air flow into the air inlet, and a gas sensor positioned within the air channel. The air scoop is positioned to receive and capture air flow of at least one of the plurality of propellers to induce the air flow into the air channel and toward the gas sensor.

In certain embodiments, the microcontroller controls the position of the air scoop via an actuator to optimize air flow into the air channel and to the gas sensor.

In certain embodiments, the multirotor drone further comprises a compression spring coupled to the main body and to the air scoop and operative to provide a biasing force against the scoop closing over the air inlet completely, and a drag flap coupled to the air scoop external to the surface of the main body, wherein the drag flap imparts a rotational moment to the air scoop which tends to close the air scoop over the air inlet when exposed to air flow above a prescribed magnitude.

The multirotor drone can also include at least two legs and respective retraction shafts into which the at least two legs retract, the legs being configured to retract into the respective retraction shafts in response to contact with a surface upon landing. The air scoop can comprise first and second arms, the first arm positioned adjacent at least one of the retraction shafts and mounted for pivotable motion in response to retraction of the respective leg into the adjacent retraction shaft during a landing, and the second arm being positioned adjacent to the air inlet and arranged to pivot outwardly to expose the air inlet as the first arm pivots during the landing.

In certain implementations, at least one of the propellers is pivotable to a position in which air flow generated by the propeller is directed normally toward the air inlet and the air channel to increase air flow toward the gas sensor.

The air inlet and the air scoop can be positioned so as to receive air flow from at least two propellers of the multirotor drone.

In certain embodiments, the multirotor drone further comprises at least one additional sensor configured to detect a reference gas.

In another aspect, the present disclosure also provides a method for increasing air flow to a gas sensor of a multirotor drone having a main body and a plurality of propellers. The method comprises arranging the gas sensor within an air channel embedded inside the main body of the drone, the air channel having an opening at a surface of the main body, mounting an adjustable air scoop adjacent to the air inlet. The air scoop is adjustable to be selectively positioned to receive air flow generated by at least one of the plurality of propellers to direct air flow into the air channel and toward the gas sensor.

In certain embodiments, the drone further comprises an actuator coupled to the air scoop, and the method further comprises the step of actively controlling the air scoop using a microcontroller via the actuator.

In certain embodiments, the method further comprises biasing the air scoop in and open position over the air inlet, and providing a drag flap, exposed to the air flow provided by the at least one propeller, the drag flag being coupled to the air scoop and configured to force the air scoop toward a closed position against the biasing force in response to an air flow from the propeller above a prescribed magnitude.

In other embodiments, the method further comprises mechanically coupling the air scoop to landing gear of the multirotor drone such that, upon landing, retraction of the landing gear causes the air scoop to pivot into an open position.

In some implementations, the method further comprises adjusting at least one of the plurality of propellers into an orientation which induces air flow in a normal direction toward the air inlet. An additional propeller oriented to direct air flow in a normal direction toward the air inlet can also be provided.

These and other aspects, features, and advantages can be appreciated from the following description of certain embodiments of the invention and the accompanying drawing figures and claims.

DETAILED DESCRIPTION OF CERTAIN EMBODIMENTS OF THE DISCLOSURE

The present disclosure provides mechanisms for increasing and controlling air flow to gas sensors embedded in multirotor or in fixed wing drones by providing air scoops which capture propelled air flow into an air channel containing a target gas sensor. In multirotor drones, the propelled air flow is provided by positioning the air scoop within range of the air flow generated by one or more of the propellers of the drone. In fixed wing drones, the propelled air flow is provided by the flight speed of the drone itself, which causes an entrained air flow. The increased air flow to the gas sensor improves the sensitivity of the gas sensor and provides a more consistent profile of gas concentration as compared to prior art designs which employ exteriorly positioned gas sensors, such as on booms or other fixtures. In one or more of the embodiments described herein, the air channel can provide an interior shape which increases the volume of ambient air that is sampled during a given period of time. In such embodiments, the interior shape of the air channel can comprise a Venturi chamber in which there is a constriction downstream of the air inlet and ahead of an air outlet. The gas sensor can be positioned within the Venturi chamber either upstream or downstream of the constriction. As the gas sensor can experience drift and air flow characteristics which can vary, it is also important to calibrate the gas sensor. The present disclosure thus also provides several methods for calibrating gas sensors embedded in drones.

Sensitivity Enhancements for Multirotor Drone

Multirotor drones use a plurality of spinning-blade propellers to achieve flight, maneuverability, and stability. Typical models use four propellers (quadrotor) or six propellers (hexarotors). The drones come in a larger number of sizes and form factors which are classified as follows: "large" drones are between 25 kg and 150 kg in weight, "small" drones weigh between 2 kg and 25 kg, and "micro" drones weigh 2 kg or less. Many prevalent models are small or micro-drones.

Figure 1:
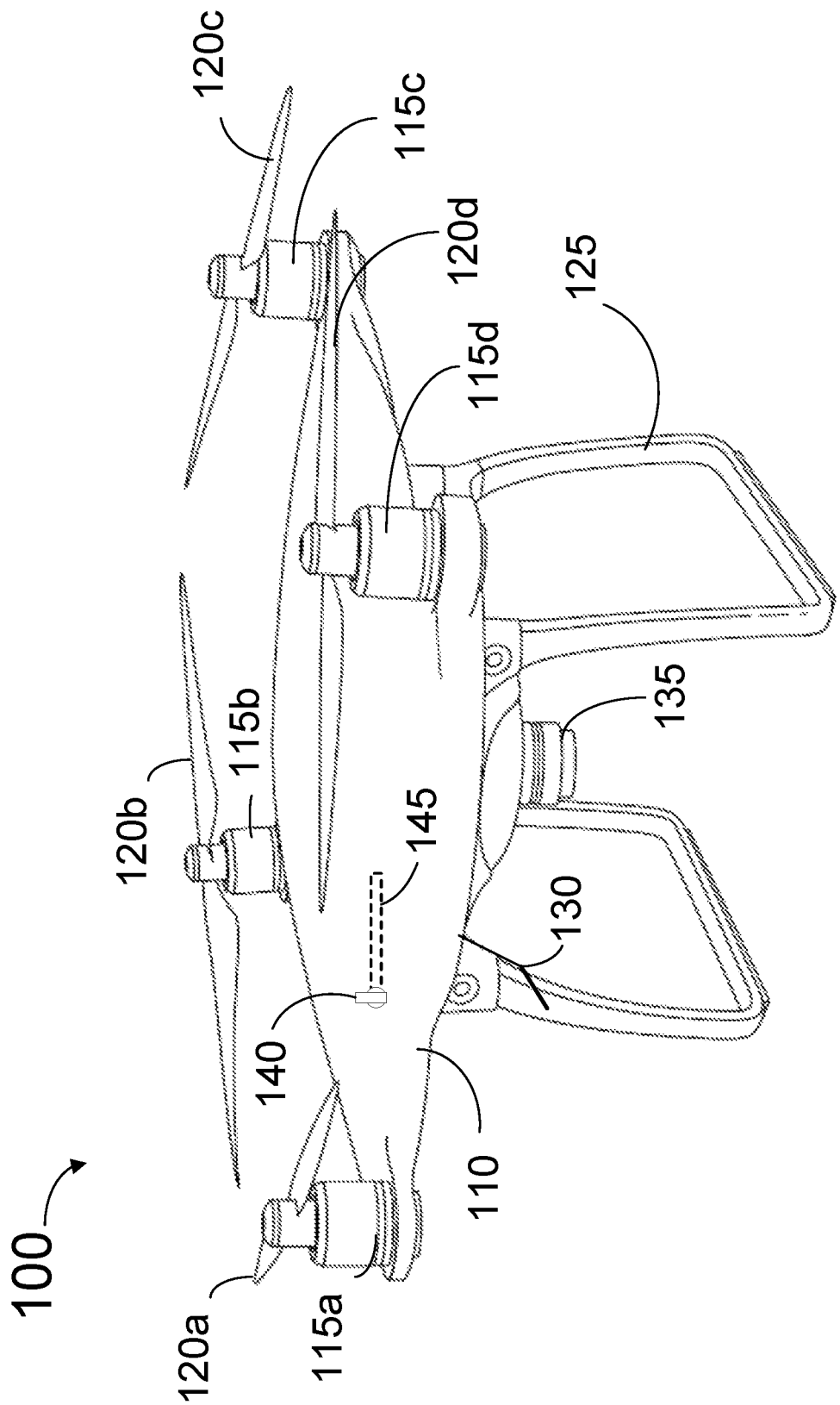
FIG. 1 is a perspective view of an exemplary multirotor drone having an air scoop for a gas sensor according to an embodiment of the present disclosure.

FIG. 1 is a perspective view of an exemplary quadrotor micro drone 100. The drone depicted is one of the Phantom models (Phantom 4) manufactured by Shenzhen DJI Sciences and Technologies Ltd., of Shenzhen, China. The Phantom 4 drone is about 1.4 kg and can reach flight speeds of 44 mph. It is understood that the specific drone size and form factor shown in FIG. 1 is merely exemplary, and the principles of the present disclosure can apply to any drone designs and sizes subject to the conditions discussed below.

The drone 100 comprises a main body 110 that houses electrical and electronic components that are used to operate the drone. In the exemplary drone 100, the body is somewhat pillow-shaped with a wide midsection narrowing toward the periphery. Arranged at each of the corners of the top of body 110 are rotary motors 115a, 115b, 115c, 115d. Propeller rotors 120a, 120b, 120c, 120d are positioned on and coupled to each of the respective motors 115a, 115b, 115c, 155d. Diagonally opposite motors 115a/115c and 115b/115d create rotation in the same direction (clockwise or counterclockwise) while the first and second pairs create rotation in the opposite direction from each other to complement each other. Motors 115a-d are operable to rotate the propellers 120a-d at selected speeds between 0 and 8000 RPM. Landing gear 125 is attached to the bottom side of the drone body 110 (opposite from the top side on which the propellers are positioned). The landing gear 125 can include a pair of flexible "legs" as shown which allow the drone to stably land on a surface. Also attached to the drone body 110 is an antenna 130 used to transmit and receive signals in a licensed communication band (typically the WiFi band, but other bands are possible). A payload fixture 135 is also coupled to the bottom of the drone body. The payload fixture 135 can be used to install additional equipment to the drone. Common examples of payload equipment include cameras, and Lidar sensors for monitoring purposes, storage containers for storing environmental samples, and grippers and mounts for package delivery, among others. Other components such as LED indicator lights (not shown in FIG. 2) are also commonly attached to the surface of the main drone body 110.

The components of drone 100 discussed thus far are typical components of known drones. The present disclosure modifies existing drones by providing an air inlet 140 and air scoop 142 to provide air flow to an internal gas sensor. The air scoop is positioned at the outer surface of the main body adjacent to the air inlet. More particularly, the air scoop is positioned to receive and capture air flow of at least one of the plurality of propellers. This positioning along the outer surface of the main body induces air flow toward the air inlet, into the air channel, and toward the gas sensor. In one embodiment, the air scoop comprises a flap, shutter or similar structure that has a first position to capture and divert air into air inlet 140 when in an "open" position, and to block air flow into the air inlet 140 when in a second, "closed" position. It is intended, however, that the air scoop be adjustable to a position in between the fully open and fully closed positions to provide a moderated air flow to the gas sensor. When the air scoop 142 is in an open position air flow from at least one of the plurality of propellers is induced or otherwise directed toward the air inlet 140 and flows into an internal air channel 145 (shown in dashed outline) leading to the gas sensor (not shown). As will be appreciated, the air channel can have an air outlet (not shown) to ensure a continuous flow of air therethrough, with the aperture at the outlet sized to meet aerodynamic constraints such as to minimize turbulence in air flow. In propeller-based drones, the air channel 145 is advantageously embedded within the main body of the drone. The air channel has an upstream end at the air inlet of the air scoop 142. It opens at the outer surface of the main body. In this or other embodiments, the air channel 145 has an interior shape which increases the volume of ambient air that is sampled during a given period of time, for instance, comprises a Venturi chamber.

As described below, the scoop can be actively (i.e., electronically) controlled or passively controlled. When actively controlled, a microcontroller, such as the microcontroller 210 discussed next or a separate controller configured by code executing therein, provides signals to a solenoid or other device to move the air scoop between its first and second positions and anywhere in between. In certain embodiments, the position to which the microcontroller moves the air scoop can be variable as a function of the volume of air being directed into the air inlet or as a function of the volume of air impinging upon the gas sensor within the air channel 145.

The inlet to the air scoop is dimensioned to be large enough to obtain sufficient incoming air flow to permit for efficient trace gas detection, but small enough to not interfere with the aerodynamics of the drone flight. In some implementations, the inlet has a cross sectional area of between 5 cm$^2$ and 1.5 cm$^2$. Further details regarding embodiments of the air scoop are discussed further below.

Figure 2:
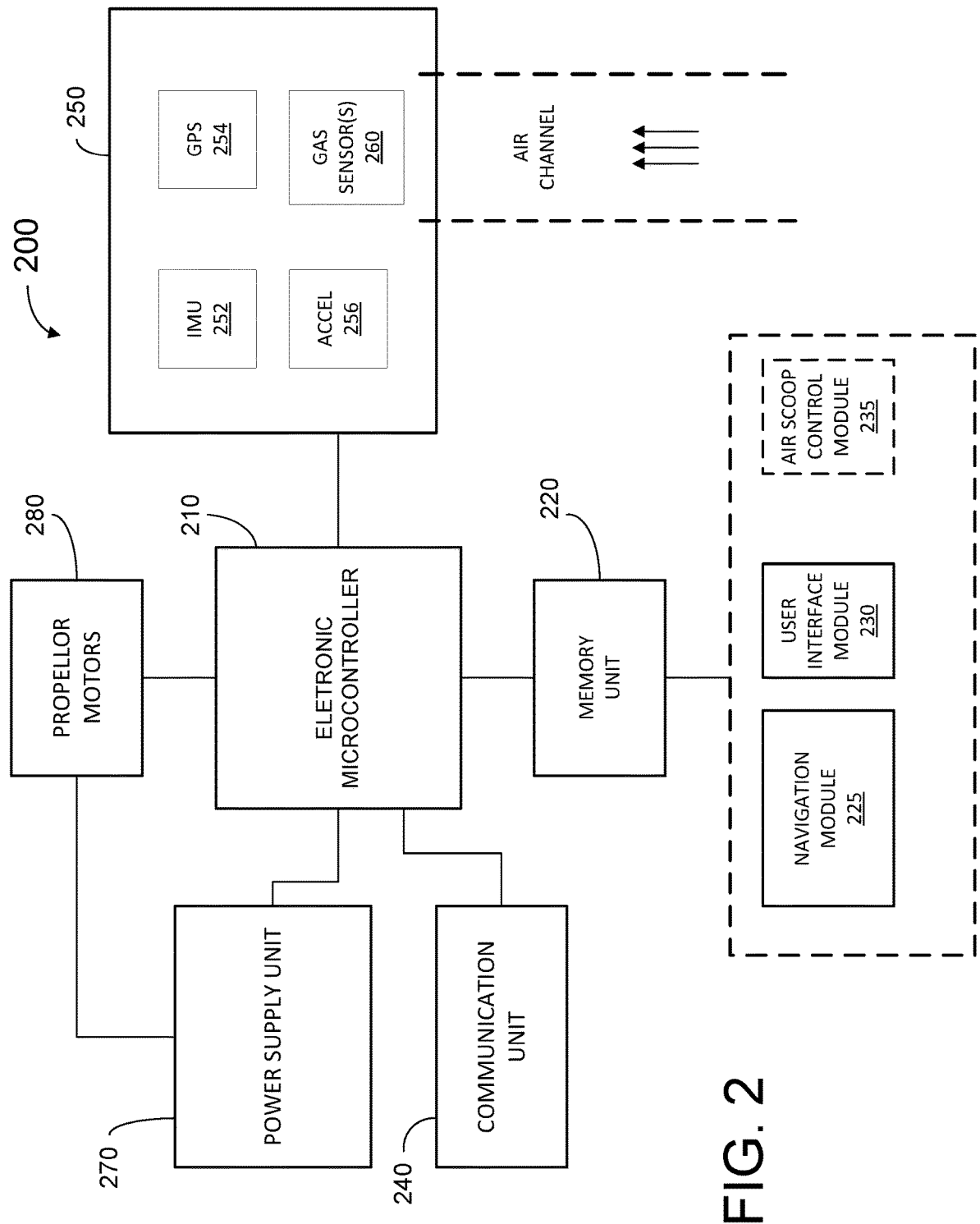
FIG. 2 is a schematic block diagram of a drone electronic control system according to one embodiment of the present disclosure.

FIG. 2 is a schematic diagram showing the electronic control system housed inside the body 110 of the drone. The drone electronic control system 200 includes a microcontroller 210, sometimes referred to as a flight controller, that can have advanced capability. Example microcontrollers that are specifically adapted for drones, and which have low latency, include Reduced Instruction Set Computer (RISC) chip sets such as e ARM®Cortex®-M7 32-bit RISC core which is rated at a speed of 216 MHz. Microcontroller 210 also encompasses cache memory and firmware that can be added to perform or optimize specific functions. The microcontroller 210 accesses and executes program modules and algorithms stored in memory unit 220 or local cache memory included in the microcontroller. Among the program modules most pertinent to this disclosure are a navigation module 225 (which can include a number of submodules), a user interface module 230, and an air scoop control module 235. (The modules are shown in a box with dash outline to indicate that they are not hardware components themselves, but rather are stored in the memory unit 220).

The microcontroller 210 is also coupled to a communication unit 240 and a suite of sensors 250, which can include a inertial measurement unit 252, a global position system transceiver 254, an accelerometer 256 and one or more target gas sensors 260 (referred to herein in the singular as "gas sensor," with no loss of generality intended). As noted above, the gas sensor is positioned in an air channel (e.g., air channel 145) that is exposed to the ambient environment via an air inlet on the surface of the main body of the drone. All of the components above receive power, directly or indirectly (i.e., through one or more intermediate components) from a power supply unit 270. In most drones, the power supply unit 270 comprises a chemical battery such as a lithium cell, but the battery unit 270 can also comprise solar cells, or a fuel cell (particularly in large drones).

The navigation module 225 includes program instructions for configurating the microcontroller 210 to execute a flight plan for the drone according to commands delivered in real time by an operator (e.g., via a mobile device), or according to a preprogrammed route. In either case, the navigation module determines how the microcontroller 210 activates the propeller motors 280 of the drone to accomplish a number of flight maneuvers such as, but not limited to, climbing, hovering, and descending in the vertical plane, as well as movements in the horizontal plane control by increasing or decreasing propeller speed of some of the propellers relative to others. The navigation module 225 also controls the pitch, roll and yaw of the drone as part of the navigation control. The user interface module 230 includes program instructions for configuring the microcontroller to interface with a drone controller application running on the operator device. For implementations in which human operators pilot the drone, the user interface module 230 processes commands received from the operator device for drone flight direction.

In accordance with a salient aspect of one aspect of the present disclosure, the air scoop control module 235 includes program instructions for configuring the microcontroller 210 to operate (e.g., open or close) the air scoop 142 to enable air capture air into the air channel 145 to reach the gas sensor 260, or otherwise, to moderate or prevent air flow into the air channel. When the microcontroller 210 executes the instructions of the air scoop module 235, the microcontroller determines the next adjustment to the position of the scoop (via an actuator mechanism that responds to electrical signals), and the timing thereof, based on a number of calculated factors including, but not limited to, drone body speed, individual propeller speed, gas sensor sensitivity, air mass flow, etc. to provide the greatest amount of air flow to the gas sensors consistent with propeller thrust and/or lift. In other words, there can be trade-off between gas sensor sensitivity and thrust/lift which can be accounted for in the programmed instructions utilized by the air scoop control module 235. As such, when gas sensor measurements are considered a high priority, the microcontroller can modify commands delivered to the navigation module based on input from the air scoop control module in order to increase or reduce air flow, depending on the circumstance, to provide an optimal air flow to the gas sensor.

Figure 3:
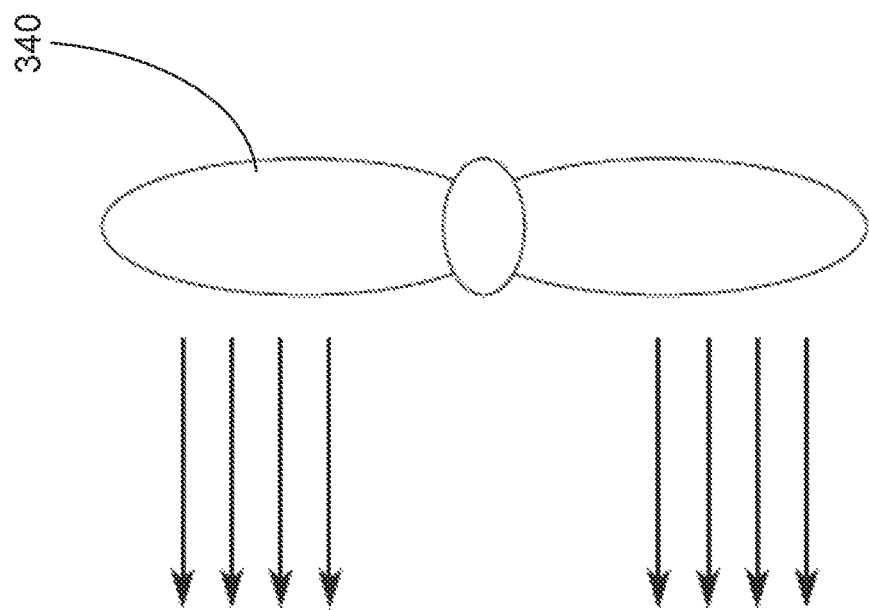
FIG. 3 is a schematic side and partial cut-away view showing an embodiment of an air scoop of a multirotor drone according to the present disclosure.
Figure 3:
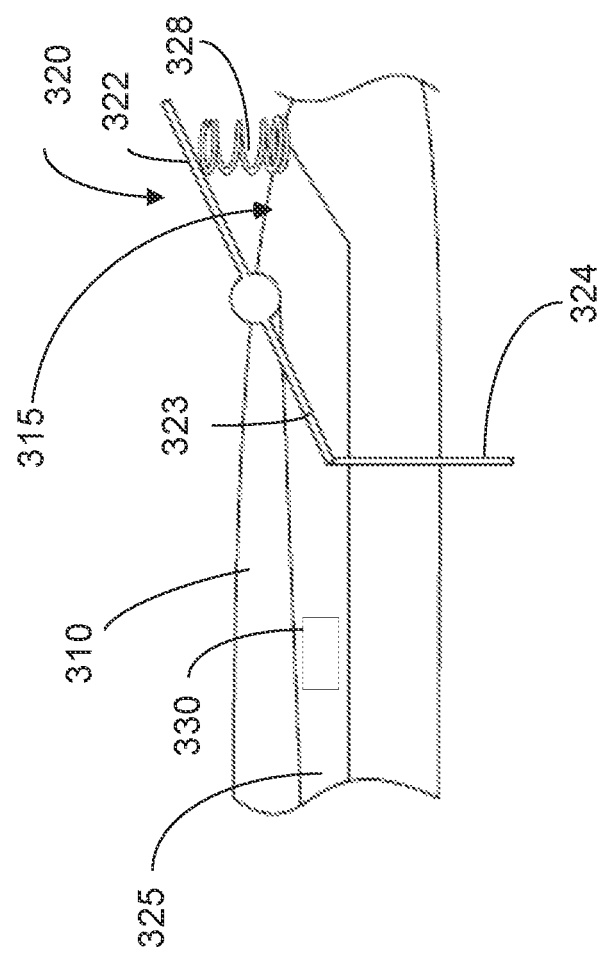

In other embodiments, the air scoop is deployed passively, meaning that the scoop opens or shuts depending upon forces acting upon it, rather than by electronic commands delivered by the microcontroller. In one embodiment, the force acting to open or maintain the scoop in an open state is inversely proportional to propeller thrust. In such embodiments, it can be helpful to reduce full propeller thrust during air gas measurements. FIG. 3 is a schematic view of an embodiment of an air scoop mechanism according to the present disclosure. As shown, main body of the drone 310 includes air inlet 315, air scoop 320 and air channel 325. The air channel can have an air outlet (not shown) to ensure a continuous flow of air therethrough, with the aperture at the outlet sized to meet aerodynamic constraints such as to minimize turbulence in air flow. The air scoop 320 is a lever-like structure that has a front section 322 that extends over the drone body and is dimensioned to be able to cover the air inlet 315 when positioned flush against the main body of the drone. A rear section of the air scoop 323 is coupled to a drag flap 324. A compression spring 328 is positioned between the front section of the air scoop 320 and the drone body 310. The compression spring is coupled to the main body and to the air scoop and is operative to provide a biasing force against the scoop closing over the air inlet completely. In such embodiments, the compression spring biases the front section in an "open" position and against shutting flush against the drone body. A gas sensor 330 is positioned downstream (in the direction of air flow) within the air channel 325 inside the main body 310 of the drone. In some implementations, the gas sensor 330 can be positioned 2 to 6 cm within the air channel 325, as measured from the air inlet 315, to achieve more laminar airflows, to minimize mechanical oscillations, to minimize other forces that can be experienced by the gas sensor, or in view of a combination of these considerations. In addition, additional sensors (not shown) can be included in the air channel for calibration purposes as discussed below. A propeller 340 is shown to the right, with lines emanating from the propeller indicating the force of air flow generated by the propeller 340. As shown, the air channel is oriented largely tangential to the direction of the air flow stream generated by propeller 340 but receives at least a portion of the air flow which enters the channel. The front section 322 of the air scoop is positioned directly in the air flow and is deployed to divert a portion of the air flow from the propeller into the air channel 325. In this or other embodiments, the air channel 325 has an interior shape which increases the volume of ambient air that is sampled during a given period of time, for instance, comprises a Venturi chamber. As will be appreciated, the air channel can have an air outlet (not shown) to ensure a continuous flow of air therethrough, with the aperture at the outlet sized to meet aerodynamic constraints such as to minimize turbulence in air flow.

As FIG. 3 illustrates, a moderate force of air flow generated by propeller generates a rotational moment on the front section 322 of the air scoop, acting in a counterclockwise direction away from the spring toward a more "open" position. The compression spring adds a force in the same direction. Conversely, at high air flow speeds, namely those above a prescribed magnitude, there is a countervailing rotational moment on the drag flap 324 which acts in a clockwise direction The clockwise moment on the drag flap 324 is transmitted to the rear section 323 of the air scoop which acts to move the front section 322 clockwise against the force of the compression spring 328, reducing the exposed area of the air inlet 315. In some embodiments, the drag flap 324 is significantly larger than the air scoop. For example, the drag flap is twice the size of the air scoop in one embodiment. Such an arrangement has the drag flap providing a stronger force than the counteracting forces of the air scoop and spring 328. This maintains the air channel closed. For example, at hovering speeds, the air flow can be high enough for forces on the drag flap 324 to close the front section of air scoop 322 over the air inlet. Whereas, after landing, the air flow provided by the propellers is low enough to keep the air scoop open, while still providing sufficient air flow to the gas sensor. Alternatively, the size and angle of the drag flap 324 and front section of the air scoop 322, and the stiffness of the spring 328 can each be selected to ensure that the air scoop is partially open at hovering speeds, closed at active flight speed, and fully open when the drone is landed. The angle of the drag flap provides moderation of the open/closed relationship of the air scoop by decreasing the amount of airflow it is in contact with as it closes, which provides an additional control over the air scoop in regard to it opening partially.

One of the objectives of this mechanism is to provide a moderated, stable air flow and pressure in all types of flight conditions, that is sufficient for the gas sensor to make sensitive measurements but is not so great as to potentially damage the gas sensors due to overly flow speed or pressure above the prescribed magnitude. The mechanism also helps in reducing the range of calibration required, as it acts as a passive control feature that reduces the range of possible air flows and pressures. More generally, the spring can be arranged to keep the scoop at least partially open against antagonistic forces provided by the drag levers at the back of the scoops, which tend to close the scoops at higher air speeds.

The air scoop mechanism shown in FIG. 3 can be deployed mid-flight in order to increase detection in specific times or areas or can be deployed during a landing while the propellers are still in operation. The propelled air flow into the air scoop increases gas detection in a specific area. The microcontroller 210 or other controller can be configured by code executing therein to make adjustments to the air scoop position as a function of air flow from the propeller being above a prescribed value stored in the memory unit 220.

Alternatively, passive control of the air scoop can be based on magnetic forces. The propellers can be made from or include conductive materials that create a magnetic field while they are spinning, in proportion to their speed. The air scoop can be designed to open or close at a threshold average propeller speed.

Figure 4:
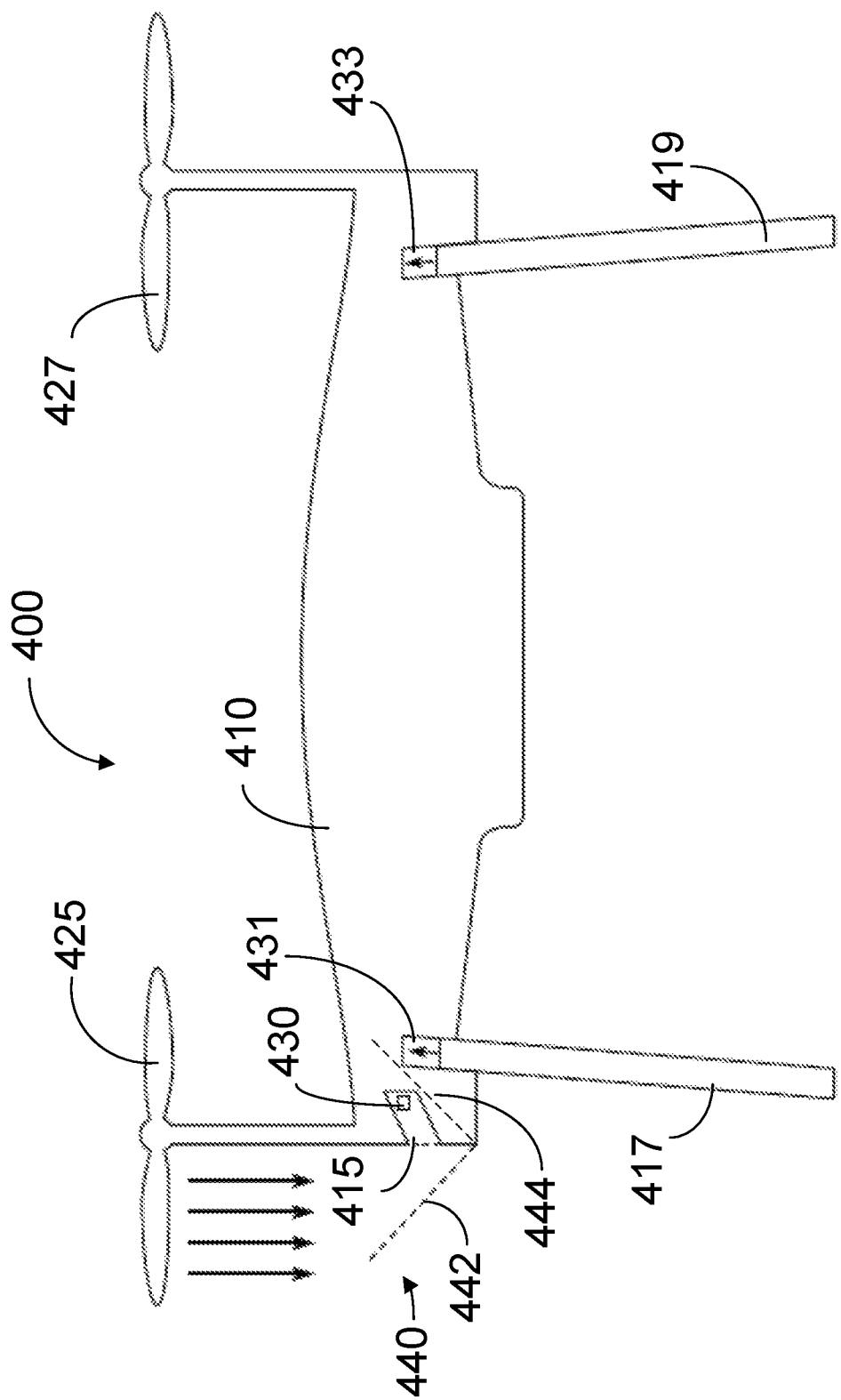
FIG. 4 is a schematic view of an embodiment of an air scoop mechanism according to the present disclosure.

FIG. 4 is a schematic view of another embodiment of an air scoop mechanism according to the present disclosure. The mechanism illustrates in FIG. 4 is adapted to be deployed when the drone lands upon surface. Drone 400 includes a main body 410, an air channel 415 positioned at the side of the main body, landing gear including retractable legs 417, 419 and propellers 425, 427. A gas sensor 430 is positioned in the air channel 415. The air channel can have a particular shape to increase the volume of ambient air that is sampled during a given period of time, for instance, a Venturi chamber shape. The air channel also can have an air outlet (not shown) to ensure a continuous flow of air therethrough, with the aperture at the outlet sized to meet aerodynamic constraints such as to minimize turbulence in air flow. The main body 410 also includes retraction shafts 431, 433 into which the landing gear legs 417, 419 retract into the respective retraction shafts in response to with a surface upon landing. An air scoop 440 is positioned on a side of the main body 410. The air scoop 440 comprises several segments. In the illustrated embodiment, the segments are L-shaped. More generally, however, the air scoop 440 has an upper segment 442 and a lower segment 444 positioned in, and pivotable within, a hollow channel within the drone (the channel is not explicitly shown in the view of FIG. 4) coupled to retraction shaft 431. The upper segment 442 is biased by a spring 445 to stay in position flush against the side of the main body in the absence of a counteracting force. The lower segment 444 has at least a section positioned within retraction shaft 431. In operation, upon landing, leg 417 is forced upwards and enters retraction shaft 431 and impinges upon the lower segment 444 of the air scoop. The forcible contact of landing gear leg 417 on lower segment 444 causes the air scoop as a whole (both segments 442, 444) to pivot counterclockwise against the biasing force of the spring coupled to the upper segment 442. In other words, the lower segment 444 pivots in response to the retraction of the leg 417, causing movement of the upper segment 442 against the biasing spring or any other element which normally retains the air scoop in a position which closes or reduces air flow into the air channel 415. More generally, the present disclosure also envisions other mechanisms to translate the normal forces transmitted upon landing into a force that opens an air scoop. Importantly, the mechanism operates to open the scoop which propeller 425 (at least) is in operation so that the air flow into the scoop, and to the gas sensor therein, is increased.

Figure 5:
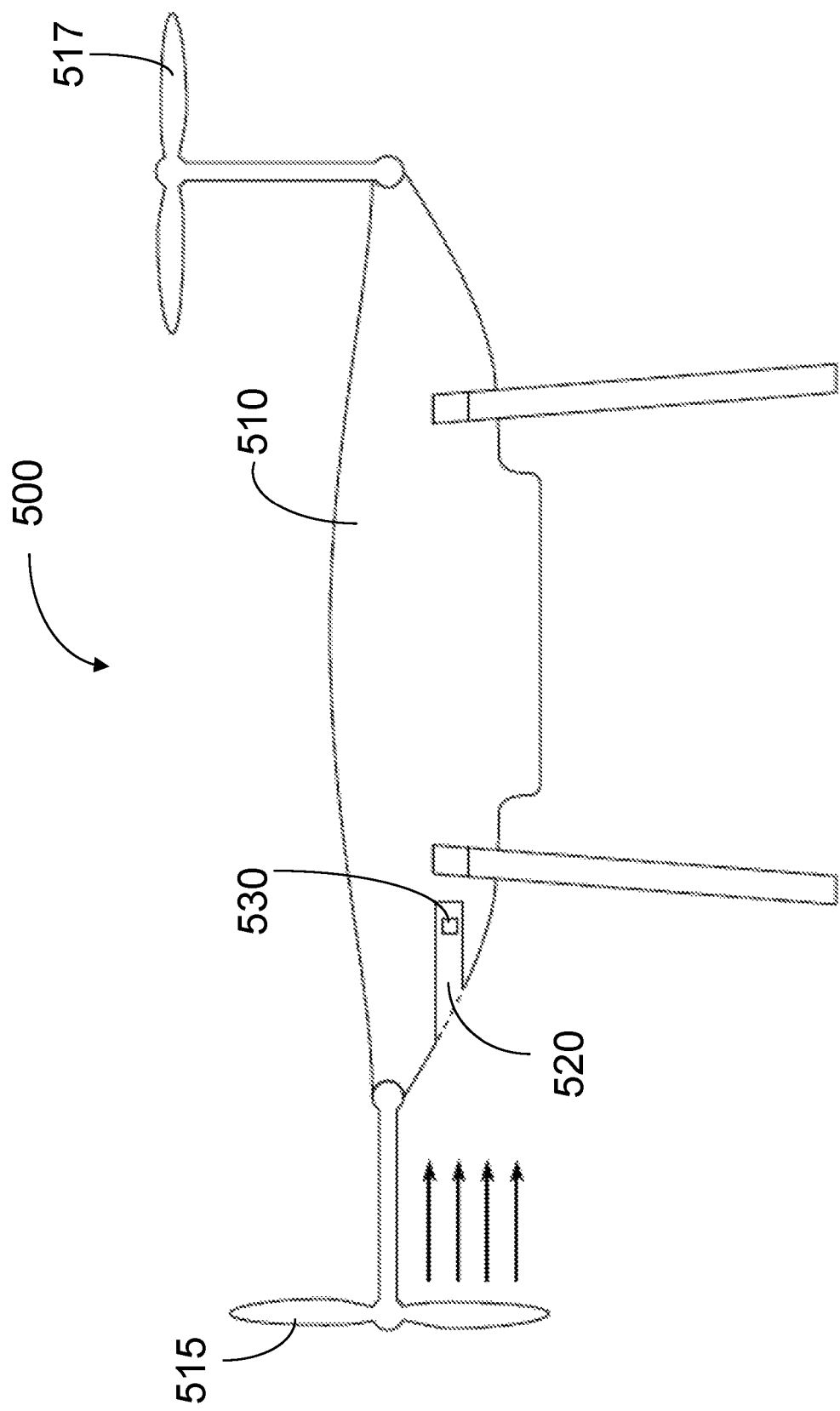
FIG. 5 is a schematic diagram illustrating another embodiment of a passive air scoop mechanism according to the present disclosure.

FIG. 5 is a schematic diagram illustrating another embodiment of a passive air scoop mechanism according to the present disclosure. Drone 500 includes main body 510 and propellers 515, 517 coupled to horizontal edges on the top of the main body. One side of the main body includes an air channel 520 having an inlet at a surface of the main body which channel contains a gas sensor 530. In this embodiment, propeller 515, on the same side of the main body as the air channel, can be freely pivoted at least ninety degrees. The propeller 515 can thereby pivot from a normal flight position in which propeller 515 is positioned over the top of the main body, to a "perpendicular" position ninety degrees counterclockwise at the side the main body. In the perpendicular position, air flow generated by propeller 515 is oriented normally to the face of the air inlet and is directed into the air channel 520. While only one propeller 515 is shown pivoted in FIG. 5, in some embodiments, other propellers can also be pivoted to provide air flow directly to the air channel 520. The embodiment depicted in FIG. 5 has the advantage that the pivoted propeller can provide air flow while the drone is not in flight. As will be understood, the aperture of the air channel 520 can be at other orientations and the pivoting of the propeller 515 need only be sufficient to adjusts from a first, flight-position suitable for navigating the drone 500 to an air-channeling position when the drone is stationary (i.e., after landing) in order to increase air flow into the air channel 520 and toward the gas sensor 530. As will be understood, the air channel 520 can have an interior shape which increases the volume of ambient air that is sampled during a given period of time, for instance, comprises a Venturi chamber. Also, as will be appreciated, the air channel can have an air outlet (not shown) to ensure a continuous flow of air therethrough, with the aperture at the outlet sized to meet aerodynamic constraints such as to minimize turbulence in air flow. In embodiments in which the propeller pivots to provide airflow into the air channel 520 and toward the gas sensor 530, the air channel is preferably on a front surface of the drone as taken in the direction that the drone is normally flown in order to catch air and passively couple it into the air channel as the drone moves in the normal direction during flight.

In a related embodiment to that shown FIG. 5, in which one or more propellers are activated while the drone has landed is substantially stationary, the gas sensor can be placed on the external surface of the drone body rather than in a channel embedded in the main body of the drone. The gas sensor can be placed on the surface indicated by the direction in which the drone is usually flown to capture air flow.

Enhancements for Fixed Wing Drones

Figure 6:
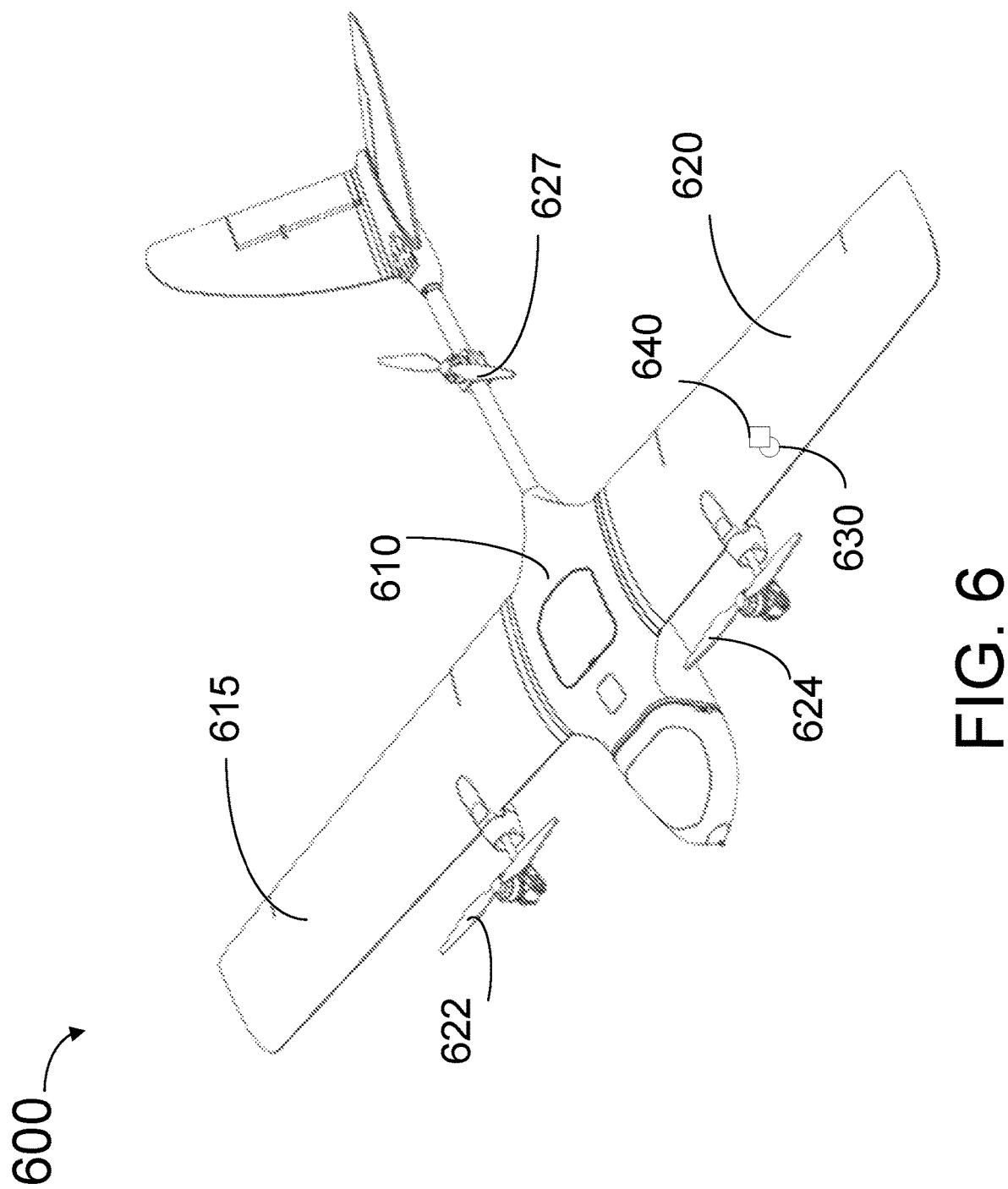
FIG. 6 is a perspective view of an exemplary fixed wing drone having an air scoop for a gas sensor according to an embodiment of the present disclosure.

While the embodiments discussed above pertain to multirotor drones, aspects of the present disclosure also apply to fixed wing drones. An exemplary fixed wing drone is illustrated in FIG. 6. The fixed wing drone (FW drone) 600 comprises a main fuselage body 610, wings 615, 620 which extend from lateral sides of the fuselage body 610, front propellers 622, 624 and rear propeller 627, among other components. In accordance with another salient aspect of the disclosure, an air inlet 630 and air scoop 640 are shown on the wing 620. In an alternative arrangement, the air inlet and air scoop can be on the central fuselage. In either case, the inlet is in fluid communication with an embedded air channel. As will be appreciated, the air channel can have an air outlet 670 (see FIG. 7) to ensure a continuous flow of air therethrough, with the aperture at the outlet sized to meet aerodynamic constraints such as to minimize turbulence in air flow. It is noted that the size of the inlet and scoop are enlarged for illustrated purposes and are not shown to scale.

As will also be appreciated, the notion of a FW drone 650 can comprise a tailless construction, the so-called "flying wing" variety, as opposed to the version illustrated in the figures. Such a construction includes an aircraft body having the outer surface referred to above with the air inlet 630 and air scoop 640, and the air channel embedded within the aircraft body. The body and wing are integral, for instance, as in the Northrop B-2 stealth bomber.

Figure 7A:
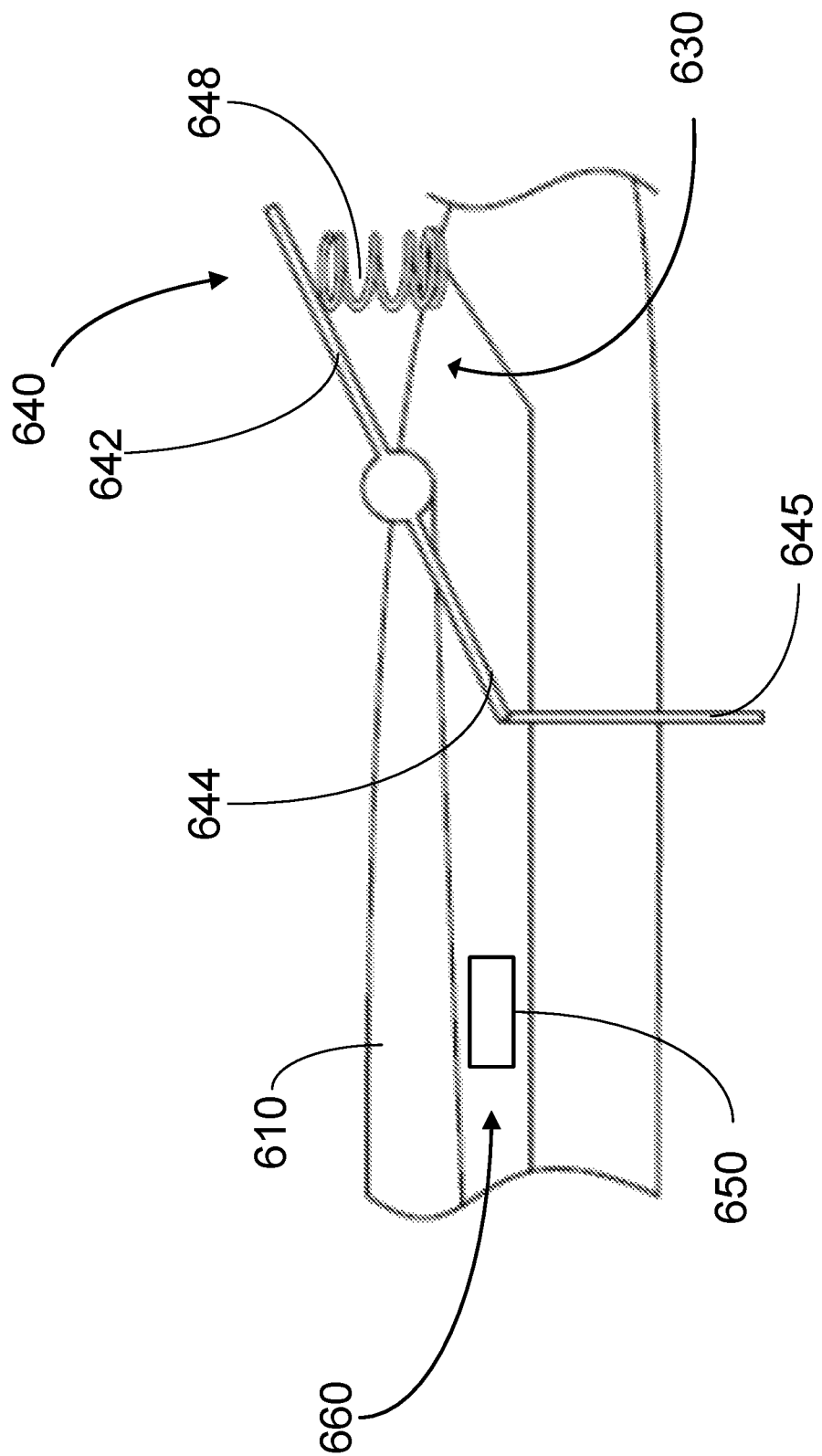
FIG. 7A is a schematic view of an embodiment of an air scoop mechanism for a fixed wing drone according to the present disclosure.
Figure 7B:
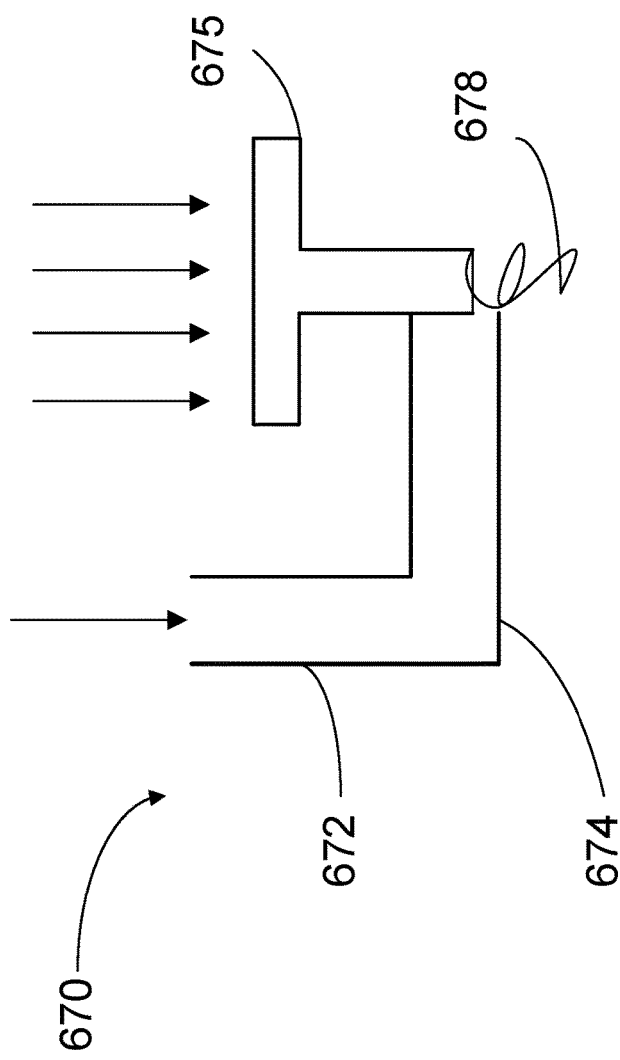
FIG. 7B is a schematic view of another embodiment of an air scoop mechanism for a drone according to the present disclosure.

The FW drone 650 includes an electronic control system, similar to that shown in FIG. 2 and described above, with the difference that the navigation module will be configured differently by the executing code because the flight characteristics of the FW drones differ from those of multirotor drones. The control system can be mounted within either the fuselage or at least one of the wings. FIG. 7A shows an embodiment of an air scoop mechanism which can be incorporated on either the fuselage body 610 or wings 615, 617 of the FW drone 600. The air scoop mechanism can be positioned on the front or rear of either component, with due consideration given to aerodynamic factors specific to each drone design that can cause certain positions for the air scoop to be more advantageous than others. The air scoop mechanism shown in FIG. 7A is similar to the air scoop mechanism shown in FIG. 3, discussed above, but does not rely upon the direct air flow generated by a propeller. The mechanism includes an air channel 660 embedded in the fuselage 610 that is exposed to the environment via the air inlet 630. However, air scoop 640 which comprises an adjustable, pivotable flap, shutter or similar structure that, depending upon its position, is provided to selectively block or open the air inlet 630 to the air channel 660. The air flow into the air channel can be changed or impeded altogether by the air flap, thus allowing the drone to minimize exposure of its onboard gas sensor until the drone has reached an area of interest where gas sampling is required. Additionally, by avoiding the scooping of air when sensing is not needed, drag is reduced which is helpful to preserve power for longer flights.

In the embodiment shown, the air scoop 640 comprises a front section 642 which extends outwardly and is dimension to cover the air inlet 630, and a rear section 644 which either extends to or is coupled to a drag flap 645. The front section is biased to against closing by a spring 649. As illustrated, the spring 649 is a compression spring. The air scoop 640 and drag flap 645 are provided and function similarly the embodiment shown in FIG. 3 to moderate air flow into the air channel 660. In some embodiments, the gas sensor 650 can be positioned 3 to 6 cm within the air channel 660 as measured from the air inlet 630 to ensure sufficient air flow without undue exposure to the force of the air flow at the gas sensor. The air scoop 640 can be actively (electronically) or passively controlled. A compression spring (not shown in FIG. 6) can be included to bias the air scoop 640 toward an open or closed position, depending on the embodiment.

The forward flight of the FW drone 600 tends to enhance air flow into the air inlet 630. Forced air is channeled past the gas sensor in such a way as to increase air flow or pressure. This, in turn, increases the volume of ambient air that is sampled during a given period of time. Air flow to the gas sensor via the air channel can be increased, reduced, or stopped depending on changes in the position of the air scoop 640. The air scoop has a section which is positioned adjacent the inlet to the air channel. The air scoop is adjustable between a first position in which air is captured during forward flight of the drone and diverted into the air inlet and, thereby, to the air channel, and a second position to block air flow into the air inlet.

The air scoop can be configured in different ways in various embodiments consistent with the present disclosure. Thus, for instance, in FIG. 7B, an air scoop 670 is embodied as a L-shaped air channel having two air channel arms 672, 674 connected at an elbow. In some implementations, the entire air channel is embedded inside the drone wing or body. Alternatively, part of air channel arm 672 can extend outwardly from the surface of the drone wing or body. As the drone flies through the air, air passes into an inlet and through the first air channel arm 672 of the scoop. The perpendicular air channel arm 674 is gated by a valve 675 coupled to a compression spring 678, illustrated schematically, that biases the valve 675 to be in an open position. A gas sensor (not shown) is positioned downstream of the valve, that is, it is further away from the inlet and the air channel arm 672. The valve can be T-shaped, as shown, having a bearing surface (e.g., the crossbar if T-shaped). The valve has a component that is exposed to air flow. In operation, as if the drone reaches a threshold air speed, the force of the air flow presses down on the crossbar or other bearing surface of the valve 675, tending to close the valve and reduce or completely prevent air flow through the perpendicular air channel arm 674, thus acting to passively control the airflow past the gas sensor.

Figure 7C:
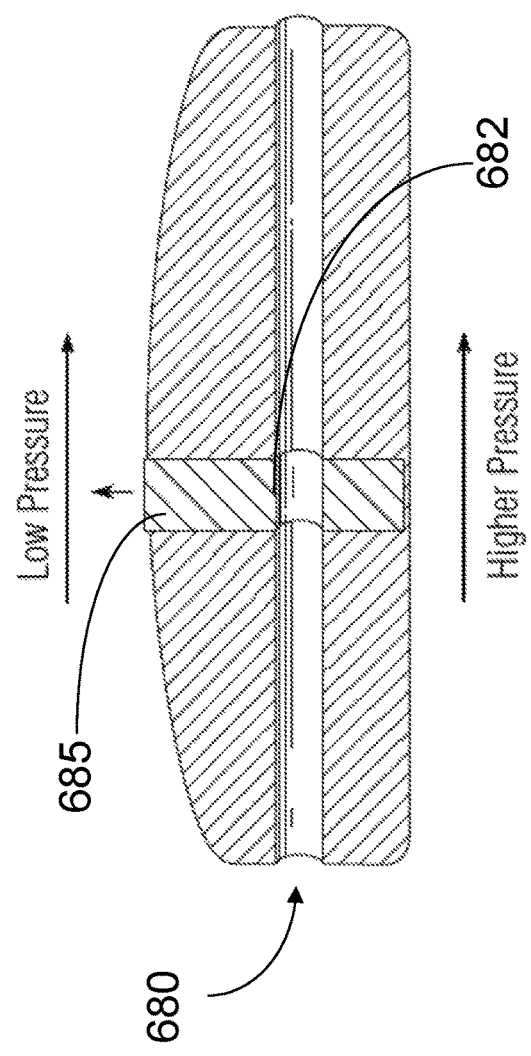
FIG. 7C is a schematic view of a further embodiment of an air scoop mechanism for a drone according to the present disclosure.

FIG. 7C illustrates another embodiment for controlling air flow to a gas sensor of a drone. During flight, the airfoil shape of the wings of fixed wing drones can create an air pressure differential between the top and bottom of the wings, as is a known principle which enables airplanes to fly. This principle can be used as a mechanism to control air flow to a gas sensor.

Thus, as shown in FIG. 7C, a wing includes an embedded air channel 680 oriented longitudinally through the wing. A valve 682 is positioned within the air channel. A pressure sensitive linking element 685 is coupled to the valve. In some embodiments, the linking element is positioned near the top of the wing. The linking element 685 is constructed so as to respond to the pressure differential between the top and bottom of the wing during flight. The pressure differential lifts the linking element 685, which in turn pulls the valve 682 to block and reduce air flow through the air channel 680. In some embodiments, a biasing spring (not shown) is positioned to bias the valve to return to an open position. A mechanical stop can also be coupled to the valve to limit upward motion of the valve 682. The linking element 685 can be coupled to the valve in such manner that the motion of the valve is amplified in comparison to the linkage motion due to the pressure differential. In certain embodiments, the linking element 685 can be positioned distally at a different location of the wing from the valve.

In some embodiments, the air scoop module is configured to actively control the air scoop to close in order to reduce drag when the drone is not in an area requiring gas detection, or when the air flow to the gas sensor does not require enhancement, such as when improved measurement sensitivity is not needed. The air scoop module can be configured to open the air scoops further when a trace amount of a target gas is detected in order to improve measurement sensitivity. Conversely, the air scoop module can also be configured to close the scoop when a high concentration of corrosive or explosive gas is detected as part of an abort procedure to minimize interaction between exposed electronics (e.g., of the gas sensor) potentially explosive or damaging atmosphere. More generally, the active control algorithm executed by the air scoop module via code within the processor implementing that control scheme can be configured as a closed-loop control technique which seeks to maintain an approximately constant pressure/flow rate through the channel using gas sensors in the channel, sensors out of the channel (e.g. on the wings), and/or flight controls to predict and intelligently adjust the scoop to maintain one or more specific airflow conditions. Closed-loop circuits of this type can respond dynamically to changes such as through a feedback circuit to maintain the parameter that is being controlled to remain within a prescribed tolerance, such as, with only a prescribed amount of change in pressure, flow rate, or both.

Drones can also be equipped with additional structures to ensure that flight characteristics of the drone are not deleteriously affected by the air scoop control. For example, since use of a single air scoop can create an asymmetrical drag force on the drone—depending on the position of the air scoop, in some embodiments, the drone can be equipped with additional air scoops that are controlled (actively or passively) to open symmetrically relative to the drone, the direction of flight, or both. In an alternative embodiment, other structures positioned on the drone or drone surfaces (e.g., flaps) can be either dynamically adjusted by the microcontroller or be designed to operate to compensate for the impact of the air scoop on the flight characteristics of the drone.

In active control implementations, a microcontroller can be configured be code executing therein to control the air scoop to open or close relative to flight speed to moderate the amount of air flow to the gas sensor at any given time, and at any given speed. Relatively constant air flow and pressure improves the accuracy of the gas sensor measurements as well as the need for extensive calibration across a large range of flight speeds, and in certain embodiments the microcontroller is configured to execute a control sequence that repositions the air scoop during flight to generally maintain a constant air flow and pressure at the gas sensor. The microcontroller control algorithm can incorporate additional factors such as the sensitivity characteristics of the gas sensor. Additionally or alternatively, the microcontroller can be configured to control the air scoop to open only when gas detection is desired, such as when the drone has reached a desired geophysical location, and can be moved toward a closed position to reduce drag by reducing the degree of air scooping when a sufficient volume of air is being diverted.

In passive control implementations, the air scoop can be designed to open only below a threshold flight speed, or in a variable manner based on flight speed to maintain a relatively constant quantity (flow and pressure) of air passing into the air channel and past the sensors. The latter can be accomplished using the counteracting force of the compression spring which tends to keep the air scoop in a pivoted, open position, in combination with the drag flap 680 which serves to at least partially close down the air channel at higher flight speeds.

Drone Gas Sensor Calibration

Gas sensors can have variable characteristics and their measurements can be affected by operation of the drone via factors such as air speed and pressure. Calibration is therefore required to ensure that the gas sensor used in the drone accurately measures ambient gas concentration. By increasing the air flow, pressure, or turbulence across a gas sensor, one can increase the rate of diffusion of molecules of interest into the active components of the sensor, increase the quantity of those molecules that come in contact with the active components of the sensor, or both. Regardless, this enables smaller concentrations of molecules in the ambient environment to be detected than would otherwise be possible. The increased air flow, pressure or turbulence therefore acts as a form of magnification for the gas sensor. This enhances the sensitivity of the sensor, enabling not only the detection of lower concentrations of the molecule of interest, but also the ability to obtain increased time-sensitivity in measurements of changes in concentration of a targeted gas molecule as the effective resolution increases. Another way of looking at this is to realize that enhanced air flow past the sensor effectively increases the volume of gas sampled in a given time period.

The present disclosure provides embodiments of methods for calibrating the gas sensors used in drones described above. In general, and apropos to each of the embodiments disclosed herein, the gas sensors provide a signal that must be converted to a concentration of gas measured from the ambient environment as collected through the air channels described herein.

A first method of calibration according to the present disclosure employs using one or more additional sensors that are used to detect the concentration of one or more gases that have a concentration known with a substantial degree of accuracy. The additional sensors are termed "reference sensors" and the gases of presumed known concentration are term "reference gases". A reference gas can be, for example, oxygen, carbon dioxide, nitrogen, etc. These gases are atmospheric gases which have a known concentration and variance (for example with regard to altitude). In the calibration method, referred to as the reference gas method, at least two gas sensors are employed, one gas sensor, represented by those discussed above, detects a target gas. Each additional sensor detects a reference gas. Importantly, both the target gas sensor and the reference gas sensor are arranged to experience identical air flow from propeller flow (multirotor embodiments) or flight speed (fixed wing embodiments and multirotor drones, in some cases). This can be accomplished, for example, by placing each of the sensors at a similar depth within the air channels and/or in a circumferential arrangement around a radially symmetric channel. The target sensor can then be calibrated based on the measurements of the reference sensor.

A two-dimensional grid of calibration coefficients can be created over a mapping of ranges of air speed and pressure. As noted, more than one reference sensor can be employed. Additional reference sensors can increase accuracy at the cost of extra design complexity (ensuring that all gas sensors receive similar air flow) and cost. Similarly, additional target gas sensors can be employed as well with same considerations of improved accuracy versus design costs. Furthermore, as an additional check, external measurements of reference gas can be made using environmental sensors outside of the drone, spectroscopy or sensors on the drone that are mounted outside of the air stream produced by the propellers or forward drone flight to ensure the reference remains constant.

Figure 8:
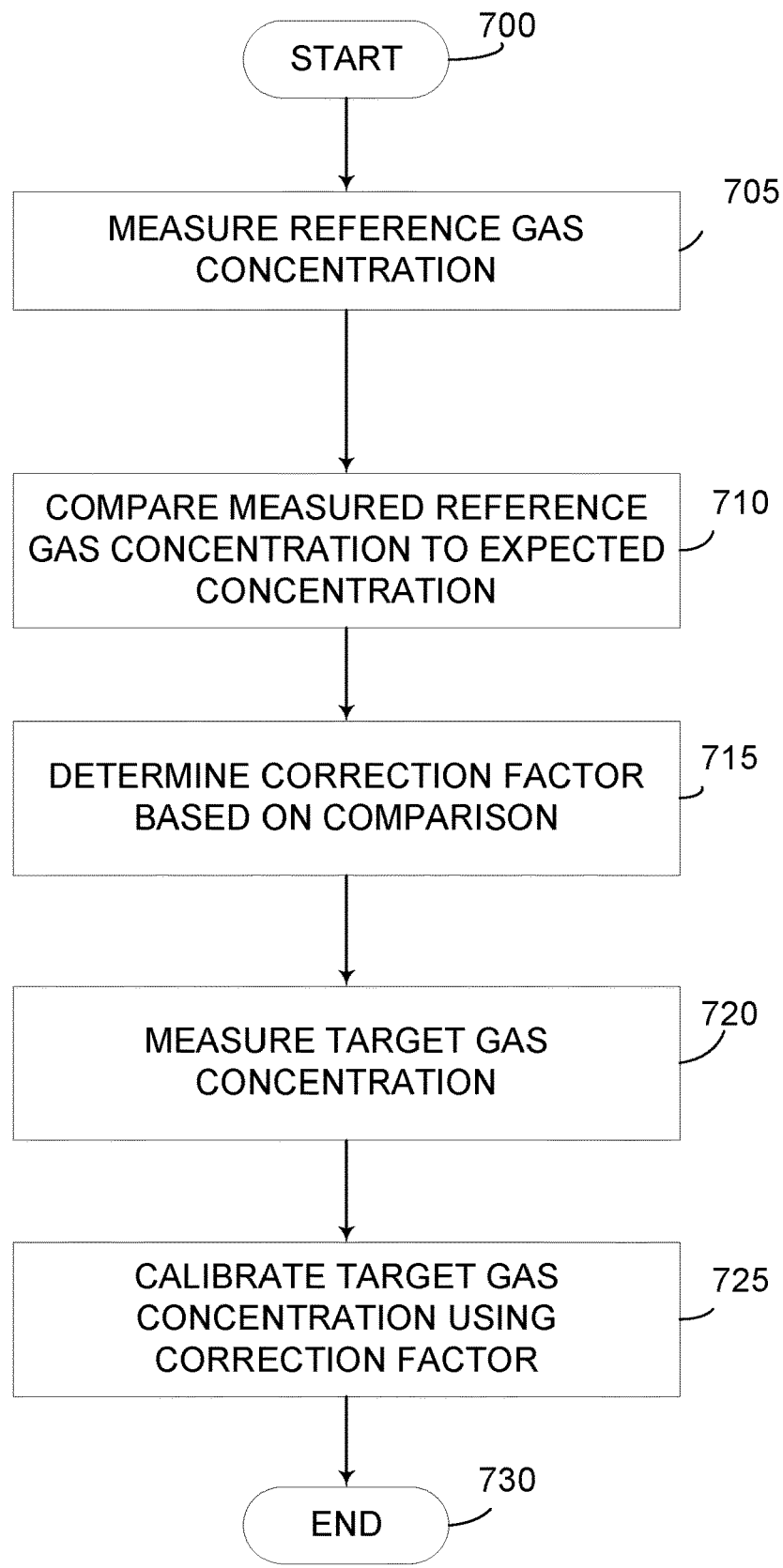
FIG. 8 is a flow chart of an embodiment of the reference gas method for calibrating a gas sensor of a drone according to the present disclosure.

FIG. 8 is a flow chart of an embodiment of the reference gas calibration method according to the present disclosure. The method begins in step 700. In step 705 measurements of a reference gas are taken by a reference gas sensor positioned to receive propeller air flow in multirotor drones or on a wing or body to experience flight-induced air flow in fixed wing drones. In step 710, the reference gas concentration is compared with an expected reference gas concentration. On the basis of this comparison, in step 715 a correction factor is determined which equalizes the measured and expected values. In step 720, the target gas is measured using a gas sensor experiencing the same air flow as the reference gas sensor. In step 725, the measured target gas concentration is calibrated using the correction factor applied to the reference gas measurement. The method ends in step 730.

A second method calibrates the target gas sensor based on detected characteristics of the air flow including mass air flow rate, pressure and or temperature (air flow calibration method). According to this method, the drone is equipped with addition sensors that can determine one or more of air flow rate and air pressure and, in some implementations temperature as well. In certain embodiments, if the air channel is configured as a Venturi chamber, air flow rate or pressure can be calculated in a conventional manner based on the air flow through that structure. At a preliminary gas sensor rating stage, concentration measurements are made of sample of known concentration at baseline values of air flow, pressure, and temperature. Additional measurements at the same known concentrations but with different air flow and pressure are performed. The additional measurements provide "deltas" indicating changes in concentration measurements solely due to the change in air flow characteristics. At this point, the behavior of the gas sensor measurements in response to air flow parameters is determined and can be used by a suitably programmed processor to perform the calibration. In some implementations, the variation can be stored as a table in memory of the electronic control system. Alternatively, the baseline gas sensor measurements can be modified based on a physical model of how variation in air flow, pressure and temperature effect the baseline values. For example, if measured air flow is higher than the baseline value, this would indicate a greater throughput of air to the gas sensor compared to the baseline which can yield a misleadingly high concentration reading. Thus, even though one of the main purposes of the present disclosure is to provide such enhanced air flow to the drone gas sensors, calibration can require the removal of at least some of the effects of enhanced flow on concentration measurements.

Figure 9:
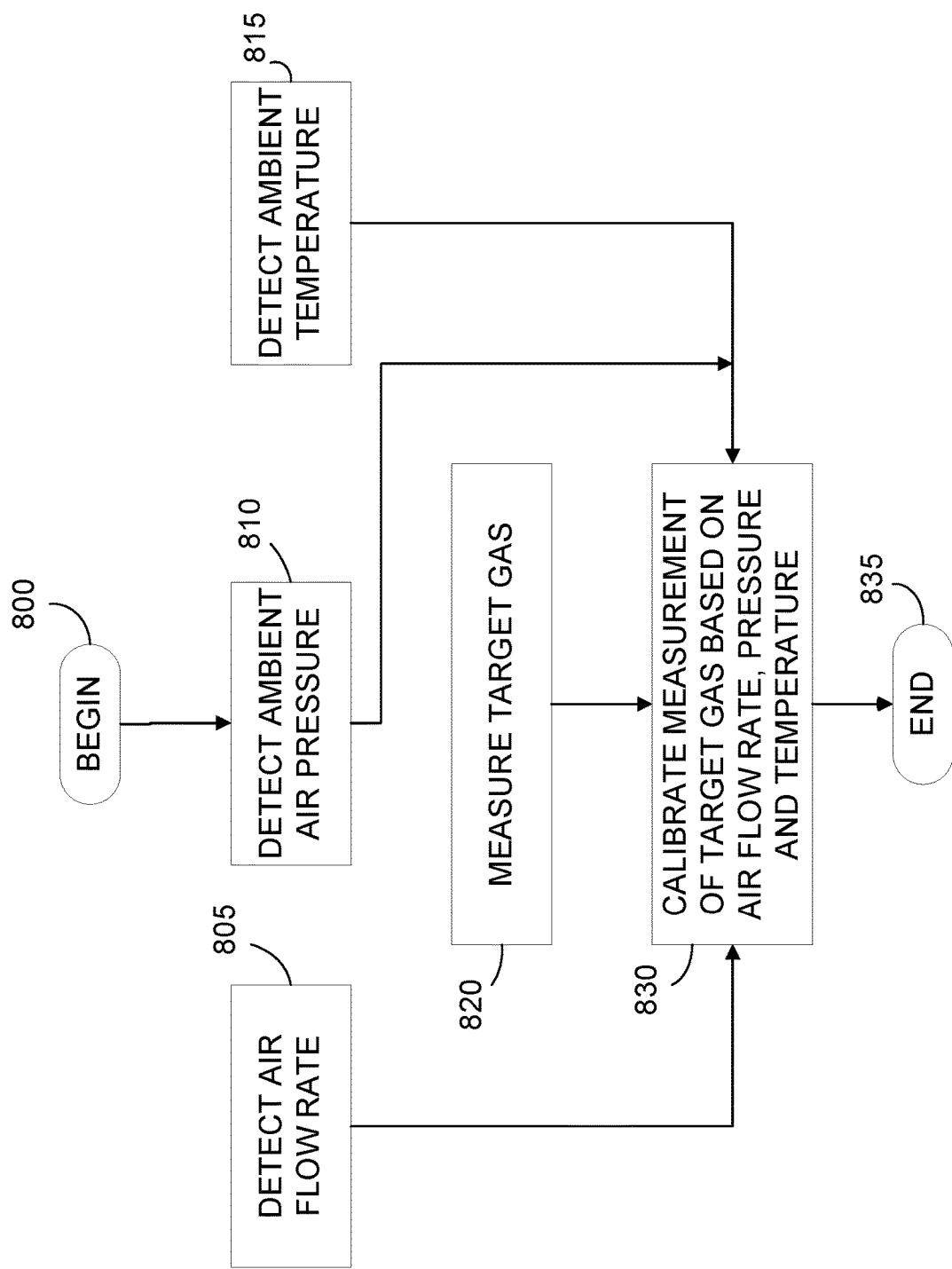
FIG. 9 is a flow chart of an embodiment of another method for calibrating a gas sensor of a drone according to the present disclosure.

FIG. 9 is a flow chart of an embodiment of the air flow calibration method according to the present disclosure. The method begins in step 800. In step 805, propelled air flow rate is detected; in step 810, ambient pressure is detected; and in step 815, temperature is detected. It is noted that in some embodiments, step 815 is excluded. Steps 805, 810, 815 can be performed simultaneously or in different order. In step 820, the gas sensor makes a measurement of the concentration of the target gas. In step 830, the gas sensor measurement is modified based on the detected air flow, pressure, and temperature. The method ends in step 835.

Another calibration method employs a dynamic equilibrium sensor in combination with a reference gas sensor. In this embodiment, unlike the first embodiment above, the calibration is automatic, and it is not necessary to apply a correction factor. The dynamic equilibrium sensor comprises a reference gas sensor, a membrane positioned downstream from the reference gas sensor that exhibits an equilibrium binding affinity based on the relative concentrations of the target and reference gases, and an additional sensor that detects the relative concentrations of the target and reference gases. The dynamic equilibrium sensor outputs a signal (e.g., optical, electrical that is an indicator of the relative partial pressures of the two gases and is independent of air flow or pressure conditions. As the reference gas concentration is known and substantially constant, the target gas concentration can be determined based on the output of the dynamic equilibrium sensor. As one example, a sensor that binds to hydrogen sulfide at a rate of ten times that rate that the sensor binds to oxygen outputs a constant signal based on relative concentrations of the two gasses that is independent of pressure or air flow.

While calibration is generally required to ensure accuracy of the target gas sensor, in some applications, such as detection of particularly hazardous gases, precise gas concentration is not of interest so much as the presence of the target gas in any magnitude. Drones can be used to monitor various locations for the presence of hazardous target gases and the control systems can be configured to generate an alarm notification upon positive detection. In such applications, the control system on-board the drone can be configured to respond to any positive sensing by the gas sensor of a specific chemical in any concentration. The response can be to abort the drone's mission, shutting down the system being observed, and so on. Sensitive gas sensors can be utilized for special-purpose (that is, specific gas constituent sensing) to support a binary response: everything is fine, or everything must stop. Such a configuration, as noted, can proceed without calibration.

It is to be understood that any structural and functional details disclosed herein are not to be interpreted as limiting the systems and methods, but rather are provided as a representative embodiment and/or arrangement for teaching one skilled in the art one or more ways to implement the methods.

It is to be further understood that like numerals in the drawings represent like elements through the several figures, and that not all components or steps described and illustrated with reference to the figures are required for all embodiments or arrangements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and "comprising", when used in this specification, specify the presence of stated features, integers, steps, operations, elements, or components, but do not preclude the presence or addition of one or more other features, integers, steps, operations, elements, components, or groups thereof.

Terms of orientation are used herein merely for purposes of convention and referencing and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

What is claimed is:

1. A multirotor drone, comprising:
   a main body having an outer surface, and an air channel embedded within the main body having an upstream end at an air inlet at the outer surface of the main body;
   a plurality of propellers coupled to the outer surface of the main body, wherein actuation of at least one of the plurality of propellers induces an air flow directed toward the air inlet and into the air channel;
   a microcontroller positioned within the main body configured to control navigation of the drone by actuation of the plurality of propellers;
   an air scoop having a section positioned at the outer surface of the main body adjacent to the air inlet, the air scoop being adjustable between a first position to capture and divert air into the air inlet and thereby to the air channel and a second position to block air flow into the air inlet;
   a gas sensor positioned within the air channel;
   a compression spring coupled to the main body and to the air scoop and operative to provide a biasing force against the scoop closing over the air inlet completely; and
   a drag flap coupled to the air scoop external to the surface of the main body, wherein the drag flap imparts a rotational moment to the air scoop which tends to close the air scoop over the air inlet when exposed to air flow above a prescribed magnitude,
   wherein the air scoop is positioned to receive and capture air flow of at least one of the plurality of propellers to induce the air flow into the air channel and toward the gas sensor.

2. The multirotor drone of claim 1, wherein the air inlet and the air scoop are positioned so as to receive air flow from at least two propellers of the multirotor drone.

3. The multirotor drone of claim 1, further comprising at least one additional sensor configured to detect a reference gas.

4. A method for increasing air flow to a gas sensor of a multirotor drone having a main body and a plurality of propellers, comprising:
   arranging the gas sensor within an air channel embedded inside the main body of the drone, the air channel having an opening at a surface of the main body;
   mounting an adjustable air scoop adjacent to the air inlet;
   biasing the air scoop in an open position over the air inlet; and
   providing a drag flap, exposed to the air flow provided by the at least one propeller, the drag flag being coupled to the air scoop and configured to force the air scoop toward a closed position against the biasing force in response to an air flow from the propeller above a prescribed magnitude,
   wherein the air scoop is adjustable to be selectively positioned to receive air flow generated by at least one of the plurality of propellers to direct air flow into the air channel and toward the gas sensor.

5. The method of claim 4, further comprising providing an additional propeller oriented to direct air flow in a normal direction toward the air inlet.

\* \* \* \* \*